United States Patent [19]

Ohinata et al.

[11] 4,152,422

[45] May 1, 1979

[54] ATTRACTANT FOR MALE MEDITERRANEAN FRUIT FLY

[75] Inventors: Kiichi Ohinata, Honolulu, Hi.; Martin Jacobson, Silver Spring, Md.; Susumu Nakagawa, Hilo, Hi.

[73] Assignee: The United States of America as represented by the Secretary of Agriculture, Washington, D.C.

[21] Appl. No.: 875,049

[22] Filed: Feb. 3, 1978

[51] Int. Cl.$^2$ ............................................. A01N 17/14
[52] U.S. Cl. ....................................................... 424/84
[58] Field of Search ........................................ 424/84

[56] References Cited

PUBLICATIONS

J. Environ. Sci. Health, A12(3), 67–78 (1977), Received: 1-6-77, Accepted 1-19-77.

Jacobson et al., J. of Med. Chem., vol. 16, pp. 248–251 (1953).

Ohinata et al., J. of Econ. Entomology, vol. 66, No. 3, pp. 812–814 (1973).

Beroza, "Pest Management with Insect Sex Attractants", A.C.S. Symposium Series 23, A.C.S. Wash., D.C., (1976), pp. 100, 148, 164, 165, 173 & 189.

*Primary Examiner*—Donald B. Moyer
*Attorney, Agent, or Firm*—M. Howard Silverstein; David G. McConnell; Theodore J. Leitereg

[57] ABSTRACT

A method for attracting male Mediterranean fruit flies is described. The attractant substance is methyl (E)-6-nonenoate and it may be used alone or in combination with (E)-6-nonen-1-ol and mixtures of fatty acids to enhance its activity and longevity.

5 Claims, No Drawings

ATTRACTANT FOR MALE MEDITERRANEAN FRUIT FLY

BACKGROUND OF THE INVENTION

1. Field of the Invention

This invention relates to and has among its objects the provision of novel compositions and methods for attracting male Mediterranean fruit flies. Further objects of the invention will be evident from the following description wherein parts and percentages are by weight unless otherwise specified.

2. Description of the Prior Art

One of the worst pests of citrus fruits is the Mediterranean fruit fly, *Ceratitis capitata* Wiedemann, commonly referred to as the "medfly." Although the medfly is currently not present in the mainland of the United States, it is abundant in Hawaii and Central America and presents a major threat to fruit production in the subtropical regions of the continent. Furthermore, the recent appearance of the medfly in Southern Mexico is cause for serious concern.

Currently, the most widely-used attractant for the male medfly is tert-butyl 4(or 5)-chloro-2-methylcyclohexanecarboxylate (trimedlure). This known lure is used in many parts of the world and is a very effective attractant for male medflies.

Recently, it was discovered that methyl (E)-6-nonenoate (MEN) was attractive and sexually excitatory to female medflies in the laboratory (M. Jacobson et al., *Journal of Medicinal Chemistry*, Vol. 16, pp. 248-251, 1973). MEN was first isolated from a highly volatile substance released from the erectile anal ampoules of male medflies. This chemical substance sexually excited and attracted virgin female medflies and was found to contain MEN as one of its constituents. These attractive substances, known as sex pheromones, are believed to originate in two glands located in the last (seventh) abdominal segment of the male medfly. The substance is apparently diffused from these glands to the surface of the erectile anal ampoule formed by pulsating pressure from the posterior portion of the rectum. Upon release, it is dispersed by air currents set up by the male's vibrating wings.

MEN was produced synthetically with the hope that it could be used to control infestations of female medflies. Indeed, the synthetic material was found to be sexually attractive to female medflies in the laboratory.

SUMMARY OF THE INVENTION

We have found that MEN is attractive exclusively to male medflies in the field; female medflies are not responsive to MEN in the wild. This result is quite surprising and unexpected for several reasons. First, MEN was isolated from a sex pheromone produced by the male medfly. Consequently, it was considered extremely unlikely that MEN would be attractive to male medflies. Second, in laboratory tests MEN was strongly attractive to both laboratory-reared and "wild"(reared out of field-infested fruit) female medflies, giving rise to the supposition that MEN would be attractive to female medflies in the field. Nonetheless, numerous field studies have established that MEN is attractive solely to male medflies.

Another advantage of the invention is that MEN should not be harmful to other animal species including humans. Thus, the safety of food supplies, of environmental quality, and of wildlife and humans is assured.

DESCRIPTION OF THE PREFERRED EMBODIMENTS

MEN has the following structure

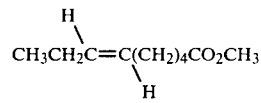

As mentioned above, it is attractive to male medflies in the wild. Thus, populations of male medflies may be manipulated or suppressed.

The compound of the invention can be used in actual practice in the field in traps. The agent may be used as is or it may be dissolved in volatile inert solvents such as liquid hydrocarbons, emulsified in water, or admixed with any other inert carrier-solid or liquid. Systems may be used wherein the compound of the invention is impregnated on a solid carrier such as paper, cloth, clay, sawdust, wood chips, or other absorbent material. The attractant may also be dispersed into the atmosphere by the use of wicks dipping into containers of the agent composition. The attractant may be used to bait traps which are provided with adhesive materials which retain insects by their stickiness. Alternatively, the traps may be provided with mechanical arrangements to prevent the exit of insects which have entered the traps. Another system is to provide the traps with toxicants to kill the insects which enter therein. Baited traps may be employed to ascertain the size and location of infestations.

Hereinabove, emphasis has been directed to the use of the composition of the invention in traps, in such a way as to concentrate the medfly population. The attractant of the invention may also be used to disperse medflies by pheromone masking. Thus, the sex life of the medflies can be controlled by keeping them from finding members of the opposite sex. For example, the atmosphere can be permeated with MEN, thus diverting the male medflies and preventing them from orienting to and inseminating females. Field trials with other insects have indicated that control of this nature over large areas may be possible with appropriate sex attractants.

The above examples are provided by way of illustration and not limitation; the attractant of the invention may be used in any way known to the art. The description provided herein shall determine the scope of the invention and variations may be made without departing therefrom.

The agent used in accordance with the invention is a known compound. MEN may be synthesized readily as follows: (E)-6-Nonenoic acid is converted to its methyl ester by treatment with aqueous methanol. The synthetic procedure is described by Jacobson in the article in the *Journal of Medicinal Chemistry* mentioned hereinabove.

It is within the compass of the invention to use MEN in combination with certain agents which enhance its activity and longevity. For example, a suitable combination in accordance with the invention is 3-4 parts of MEN, 1 part of (E)-6-nonenol, and 3 to 4 parts of a fatty acid mixture containing 26-27% octanoic acid, 38-39% decanoic acid, and 34-36% tetradecanoic acid. Also, a very effective composition of the invention may be formulated as follows: 3 to 4 parts of MEN, 1 part of (E)-6-nonenol, and 9 to 10 parts of a fatty acid mixture containing 5-6% 2-methylpropanoic acid, 1-2% 3- methylbutanoic acid, 0.1 to 1% 3-methyl-2-butenoic acid, 1-2% hexanoic acid, 1-2% 4-methyl-3-pentenoic acid, 11% octanoic acid, 16% decanoic acid, 18-19% dodecanoic acid, 14-15% tetradecanoic acid, 5-6% (Z)-9-hexadecenoic acid, 0.5-1% (E)-9-hexadecenoic acid, 14% hexadecanoic acid, 2-3% (Z)-9-octadecenoic acid, 1-2% (Z,Z)-9,12-octadecadienoic acid, and 5-6% octadecanoic acid.

EXAMPLES

The invention is further demonstrated by the following illustrative examples.

Attractiveness is relative. Accurate assessment of attractiveness depends on simultaneous comparisons amply replicated in space and time. To meet these requirements, different attractant compositions listed below were offered simultaneously to naturally occurring medfly populations. Response to attractant was quantified by the number of medflies caught on sticky traps near the attractant source. Treatments were randomly assigned to a different position before each test.

The attractants were formulated from chemicals in the pure form. The following attractant compositions were employed:
A. Methyl (E)-6-nonenoate (MEN)
B. MEN plus 15 fatty acids:

| Acid number | Acid name | Percent of total acids |
|---|---|---|
| 1 | 2-Methylpropanoic | 5.1 |
| 2 | 3-Methylbutanoic | 1.6 |
| 3 | 3-Methyl-2-butenoic | 0.4 |
| 4 | Hexanoic | 1.8 |
| 5 | 4-Methyl-3-pentenoic | 1.9 |
| 6 | Octanoic | 11.0 |
| 7 | Decanoic | 16.0 |
| 8 | Dodecanoic | 18.7 |
| 9 | Tetradecanoic | 14.3 |
| 10 | (Z)-9-Hexadecenoic | 5.2 |
| 11 | (E)-9-Hexadecenoic | 0.8 |
| 12 | Hexadecanoic | 14.0 |
| 13 | (Z)-9-Octadecenoic | 2.9 |
| 14 | (Z,Z)-9,12-Octadecadienoic | 1.1 |
| 15 | Octadecanoic | 5.2 |
|  |  | 100.0% | in the proportion of 2.9 parts of fatty acid mixture to 1 part of MEN.
C. MEN plus 3 fatty acids, namely, 6, 7, and 9, above, in the proportion of 2.7 parts of fatty acid mixture containing 26% of 6, 39% of 7, and 35% of 9, to 1 part of MEN.
D. MEN plus (E)-6-nonen-1-ol (NOL) plus 15 fatty acids as in B in the proportion of 3.6 parts of MEN, 1.0 part of NOL, and 10 parts of fatty acid mixture.
E. MEN plus NOL plus 3 fatty acids as in C in the proportion of 4 parts MEN, 1 part NOL, and 4 parts of fatty acid mixture.
F. Trimedlure.

EXAMPLE 1

A field test was conducted in a coffee orchard at Kona, Hawaii, from October 1976 to January 1977.

The attractants (1 g. samples) were placed on cotton wicks in polyethylene vial caps. The caps were placed in Jackson sticky traps, which were spaced about 10 meters apart in the test area. The tests were conducted for a period of 13 weeks and were replicated 8 times. The results are summarized in the following table; no female medflies were caught.

| Run | Attractant | Number of male medflies caught |
|---|---|---|
| A | MEN | 3117 |
| B | MEN + 15 acids | 3016 |
| C | MEN + 3 acids | 3819 |
| D | MEN + NOL + 15 acids | 4193 |
| E | MEN + NOL + 3 acids | 3682 |
| F | Trimedlure* | 3150 |

*Not in accordance with the invention but provided for purposes of comparison.

EXAMPLE 2

A field test similar to that described in Example 1 was conducted in a coffee orchard at Kona, Hawaii, in February and March 1977.

The attractants used in Example 1 were employed; these attractants were those which had been previously exposed in Example 1. As a control trimedlure was freshly applied to a cotton wick (Run F). The test was conducted for 6 weeks.

The results are summarized below; no female medflies were caught.

| Run | Attractant | Number of male medflies caught |
|---|---|---|
| A | MEN | 5103 |
| B | MEN + 15 acids | 5027 |
| C | MEN + 3 acids | 3688 |
| D | MEN + NOL + 15 acids | 2314 |
| E | MEN + NOL + 3 acids | 2767 |
| F | Trimedlure* | 4571 |
| G | Trimedlure* (freshly applied) | 7742 |

*Not in accordance with the invention but provided for purposes of comparison.

Having thus described our invention, we claim:
1. A method of attracting wild male, but not wild female, Mediterranean fruit flies of the species *Ceratitis capitata* Wiedemann, which comprises baiting a trap in an area infested with said fruit flies with an amount of methyl (E)-6-nonenoate effective to attract the wild male Mediterranean fruit flies to said trap.
2. The method of claim 1 wherein the traps are baited with 3-4 parts of methyl (E)-6-nonenoate, 1 part of (E)-6-nonen-1-ol, and 3-4 parts of a mixture containing 26-27% octanoic acid, 38-39% decanoic acid, and 34-36% tetradecanoic acid.
3. The method of claim 1 wherein the traps are baited with 3-4 parts of methyl (E)-6-nonenoate, 1 part of (E)-6-nonen-1-ol, and 9-10 parts of a mixture containing 5-6% 2-methylpropanoic acid, 1-2% 3-methylbutanoic acid, 1-2% 3-methyl-2-butenoic acid, 1-2% hexanoic acid, 1-2% 4-methyl-3-pentenoic acid, 11% octanoic acid, 16% decanoic acid, 18-19% dodecanoic acid, 14-15% tetradecanoic acid, 5-6% (Z)-9-hexadecenoic acid, 0.5-1% (E)-9-hexadecenoic acid, 14% hexadecanoic acid, 2-3% (Z)-9-octadecenoic acid, 1-2% (Z,Z)-9-octadecadienoic acid, and 5-6% octadecanoic acid.
4. A composition for attracting wild male, but not wild female, Mediterranean fruit flies of the species *Ceratitis capitata* Wiedemann, which comprises about 3-4 parts of methyl (E)-6-nonenoate, 1 part of (E)-6-nonenol, and 3-4 parts of a mixture containing 26-27% octanoic acid, 38-39% decanoic acid, and 34-35% tetradecanoic acid.
5. The composition of claim 4 which further comprises 9-10 parts of a mixture containing 2-methylpropanoic acid (5-6%), 3-methylbutanoic acid (1-2%),

3-methyl-2-butenoic acid (0.1–1%), hexanoic acid (1–2%), 4-methyl-3-pentenoic acid (1–2%), dodecanoic acid (18–19%), (Z)-9-hexadecenoic acid (5–6%), (E)-9-hexadecenoic acid (0.5–1%), hexadecanoic acid (14%), (Z)-9-octadecenoic acid (2–3%), (Z,Z)-9,12-octadecadienoic acid (1–2%), and octadecanoic acid (5–6%), and an additional 3–4 parts of a mixture containing 26–27% octanoic acid, 38–39% decanoic acid, and 34–36% tetradecanoic acid.

* * * * *